US008956295B2

(12) United States Patent
Ni et al.

(10) Patent No.: US 8,956,295 B2
(45) Date of Patent: Feb. 17, 2015

(54) SLEEP DETECTION USING AN ADJUSTABLE THRESHOLD

(71) Applicant: Cardiac Pacemakers, Inc., St. Paul, MN (US)

(72) Inventors: Quan Ni, Shoreview, MN (US); Zoe Hajenga, Minneapolis, MN (US); Douglas R. Daum, Woodbury, MN (US); Jeffrey E. Stahmann, Ramsey, MN (US); John D. Hatlestad, Maplewood, MN (US); Kent Lee, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/021,773

(22) Filed: Sep. 9, 2013

(65) Prior Publication Data

US 2014/0005503 A1 Jan. 2, 2014

Related U.S. Application Data

(60) Continuation of application No. 11/717,561, filed on Mar. 13, 2007, now Pat. No. 8,535,222, which is a division of application No. 10/309,771, filed on Dec. 4, 2002, now Pat. No. 7,189,204.

(51) Int. Cl.
*A61B 5/00* (2006.01)
*A61B 5/11* (2006.01)
(Continued)

(52) U.S. Cl.
CPC .............. *A61B 5/4815* (2013.01); *A61B 5/686* (2013.01); *A61B 5/1116* (2013.01);
(Continued)

(58) Field of Classification Search
CPC .......... A61B 5/00; A61B 5/0205; A61B 5/08; A61B 5/085; A61B 5/1116; A61B 5/1118; A61B 5/0031; A61B 5/686; A61B 5/4806–5/4818; A61B 5/021–5/024; A61B 5/72; A61B 5/7271; A61B 5/7282; A61N 1/36542; A61N 1/36585; A61N 1/36135; A61N 1/362; A61N 1/365; G06F 19/30; G06F 19/3406; G06F 19/345
USPC ......... 600/300–301, 595, 484, 324, 483, 508, 600/529–533; 607/9, 17–19; 706/46–47; 702/19; 340/575
See application file for complete search history.

(56) References Cited

U.S. PATENT DOCUMENTS 3,309,924 A    3/1967 Kolin et al.
(Continued)

FOREIGN PATENT DOCUMENTS

EP    1163877 A1 * 12/2001
(Continued)

OTHER PUBLICATIONS

Phillipson, E. A. "Control of breathing during sleep". Am. Rev. Respir. Dis. 118: 909-939, 1978.*
(Continued)

*Primary Examiner* — William Thomson
*Assistant Examiner* — Marie Archer
(74) *Attorney, Agent, or Firm* — Seager, Tufte & Wickhem, LLC

(57) ABSTRACT

Devices and methods for sleep detection involve the use of an adjustable threshold for detecting sleep onset and termination. A method for detecting sleep includes adjusting a sleep threshold associated with a first sleep-related signal using a second sleep-related signal. The first sleep-related signal is compared to the adjusted threshold and sleep is detected based on the comparison. The sleep-related signals may be derived from implantable or external sensors. Additional sleep-related signals may be used to confirm the sleep condition. A sleep detector device implementing a sleep detection method may be a component of an implantable pulse generator such as a pacemaker or defibrillator.

20 Claims, 10 Drawing Sheets

(51) Int. Cl.
  *A61B 5/085* (2006.01)
  *A61B 5/021* (2006.01)
  *A61N 1/362* (2006.01)
  *A61N 1/365* (2006.01)
  *A61B 5/0205* (2006.01)
  *G06F 19/00* (2011.01)
  *A61N 1/00* (2006.01)

(52) U.S. Cl.
  CPC ........... *A61B 5/0031* (2013.01); *G06F 19/345* (2013.01); *A61B 5/7271* (2013.01); *G06F 19/3406* (2013.01); *A61B 5/7282* (2013.01); *A61B 5/085* (2013.01); *A61B 5/021* (2013.01); *A61N 1/362* (2013.01); *A61N 1/36542* (2013.01); *A61N 1/365* (2013.01); *A61B 5/0205* (2013.01); *A61B 5/4809* (2013.01)
  USPC ........... 600/301; 600/300; 600/595; 600/484; 600/324; 600/483; 600/508; 600/529; 600/530; 600/531; 600/532; 340/575; 702/19; 607/9; 607/17; 607/18; 607/19

(56) References Cited

U.S. PATENT DOCUMENTS

| | | | |
|---|---|---|---|
| 3,522,811 A | | 8/1970 | Wingrove |
| 3,650,277 A | | 3/1972 | Sjostrand et al. |
| 3,835,864 A | | 9/1974 | Rasor et al. |
| 3,870,051 A | | 3/1975 | Brindley |
| 3,943,936 A | | 3/1976 | Rasor |
| 4,228,803 A | * | 10/1980 | Rickards .......... 607/25 |
| 4,305,396 A | * | 12/1981 | Wittkampf et al. ......... 607/25 |
| 4,312,734 A | | 1/1982 | Nichols |
| 4,323,073 A | | 4/1982 | Ferris |
| 4,365,636 A | * | 12/1982 | Barker .......... 600/529 |
| 4,390,405 A | | 6/1983 | Hahn et al. |
| 4,573,481 A | | 3/1986 | Bullara et al. |
| 4,590,946 A | | 5/1986 | Loeb et al. |
| 4,702,253 A | | 10/1987 | Nappholz et al. |
| 4,719,921 A | | 1/1988 | Chirife |
| 4,721,110 A | | 1/1988 | Lampadius |
| 4,777,962 A | | 10/1988 | Watson et al. |
| 4,782,836 A | * | 11/1988 | Alt .................. 607/19 |
| 4,784,162 A | | 11/1988 | Ricks et al. |
| 4,791,931 A | | 12/1988 | Slate |
| 4,802,485 A | | 2/1989 | Bowers et al. |
| 4,807,629 A | | 2/1989 | Baudino et al. |
| 4,819,662 A | | 4/1989 | Heil et al. |
| 4,827,943 A | | 5/1989 | Bornn et al. |
| 4,836,219 A | | 6/1989 | Hobson et al. |
| 4,846,195 A | | 7/1989 | Alt |
| 4,856,524 A | | 8/1989 | Baker |
| 4,875,477 A | | 10/1989 | Waschke et al. |
| 4,886,064 A | | 12/1989 | Strandberg |
| 4,922,930 A | * | 5/1990 | Adkins et al. .......... 607/19 |
| 4,940,052 A | * | 7/1990 | Mann et al. .......... 607/17 |
| 4,940,065 A | | 7/1990 | Tanagho et al. |
| 4,953,551 A | | 9/1990 | Mehra et al. |
| 4,958,632 A | | 9/1990 | Duggan et al. |
| 4,960,129 A | | 10/1990 | dePaola et al. |
| 4,961,423 A | | 10/1990 | Canducci |
| 4,967,159 A | | 10/1990 | Manes |
| 4,972,834 A | * | 11/1990 | Begemann et al. .......... 607/25 |
| 4,972,842 A | | 11/1990 | Korten et al. |
| 4,972,848 A | | 11/1990 | Di Domenico et al. |
| 4,982,738 A | | 1/1991 | Griebel |
| 5,010,888 A | | 4/1991 | Jadvar et al. |
| 5,024,222 A | | 6/1991 | Thacker |
| 5,040,533 A | | 8/1991 | Fearnot |
| 5,047,930 A | | 9/1991 | Martens et al. |
| 5,063,927 A | | 11/1991 | Webb et al. |
| 5,101,831 A | * | 4/1992 | Koyama et al. .......... 600/500 |
| 5,105,354 A | | 4/1992 | Nishimura et al. |
| 5,111,815 A | | 5/1992 | Mower |
| 5,133,353 A | | 7/1992 | Hauser |
| 5,144,960 A | | 9/1992 | Mehra et al. |
| 5,156,157 A | | 10/1992 | Valenta et al. |
| 5,170,784 A | | 12/1992 | Ramon |
| 5,174,287 A | | 12/1992 | Kallok |
| 5,179,945 A | | 1/1993 | Van Hofwegen et al. |
| 5,183,038 A | | 2/1993 | Hoffman et al. |
| 5,187,657 A | * | 2/1993 | Forbes .......... 600/513 |
| 5,188,106 A | | 2/1993 | Nappholz et al. |
| 5,190,035 A | | 3/1993 | Salo |
| 5,199,424 A | | 4/1993 | Sullivan et al. |
| 5,199,428 A | | 4/1993 | Obel et al. |
| 5,203,326 A | | 4/1993 | Collins et al. |
| 5,209,229 A | | 5/1993 | Gilli et al. |
| 5,215,089 A | | 6/1993 | Baker et al. |
| 5,233,983 A | | 8/1993 | Markowitz |
| 5,243,979 A | | 9/1993 | Stein |
| 5,243,980 A | | 9/1993 | Mehra |
| 5,245,995 A | | 9/1993 | Sullivan et al. |
| 5,259,373 A | | 11/1993 | Gruenke et al. |
| 5,261,400 A | | 11/1993 | Bardy |
| 5,275,159 A | | 1/1994 | Griebel |
| 5,280,791 A | | 1/1994 | Lavie |
| 5,282,468 A | | 2/1994 | Klepinski et al. |
| 5,282,839 A | * | 2/1994 | Roline et al. .......... 607/19 |
| 5,292,338 A | | 3/1994 | Bardy |
| 5,299,118 A | | 3/1994 | Martens et al. |
| 5,300,106 A | | 4/1994 | Dahl et al. |
| 5,314,430 A | | 5/1994 | Bardy |
| 5,314,459 A | | 5/1994 | Swanson et al. |
| 5,318,592 A | | 6/1994 | Schaldach |
| 5,318,597 A | | 6/1994 | Hauck |
| 5,330,505 A | | 7/1994 | Cohen |
| 5,330,507 A | | 7/1994 | Schwartz et al. |
| 5,330,515 A | | 7/1994 | Rutecki et al. |
| 5,331,966 A | | 7/1994 | Bennett et al. |
| 5,334,221 A | | 8/1994 | Bardy |
| 5,335,647 A | | 8/1994 | Brustad |
| 5,335,657 A | | 8/1994 | Terry, Jr. et al. |
| 5,351,394 A | | 10/1994 | Weinberg |
| 5,356,425 A | | 10/1994 | Bardy |
| 5,363,842 A | | 11/1994 | Mishelevich et al. |
| 5,372,606 A | | 12/1994 | Lang |
| 5,376,106 A | | 12/1994 | Stahmann |
| 5,398,682 A | | 3/1995 | Lynn et al. |
| 5,404,877 A | | 4/1995 | Nolan et al. |
| 5,411,525 A | | 5/1995 | Swanson et al. |
| 5,411,531 A | | 5/1995 | Hill et al. |
| 5,411,539 A | | 5/1995 | Neisz et al. |
| 5,411,540 A | | 5/1995 | Edell et al. |
| 5,437,285 A | | 8/1995 | Verrier et al. |
| 5,439,482 A | | 8/1995 | Adams et al. |
| 5,441,518 A | | 8/1995 | Adams et al. |
| 5,466,245 A | | 11/1995 | Spinelli et al. |
| 5,468,254 A | | 11/1995 | Hahn et al. |
| 5,483,969 A | | 1/1996 | Testerman et al. |
| 5,485,851 A | * | 1/1996 | Erickson .......... 600/529 |
| 5,487,755 A | | 1/1996 | Snell et al. |
| 5,507,784 A | | 4/1996 | Hill |
| 5,520,176 A | | 5/1996 | Cohen |
| 5,522,382 A | | 6/1996 | Sullivan et al. |
| 5,522,854 A | | 6/1996 | Ideker et al. |
| 5,522,862 A | | 6/1996 | Testerman et al. |
| 5,531,779 A | | 7/1996 | Dahl et al. |
| 5,540,734 A | | 7/1996 | Zabara |
| 5,540,735 A | | 7/1996 | Wingrove |
| 5,549,655 A | | 8/1996 | Erickson et al. |
| 5,562,711 A | * | 10/1996 | Yerich et al. .......... 607/17 |
| 5,571,150 A | | 11/1996 | Wernicke et al. |
| 5,578,061 A | | 11/1996 | Stroetmann et al. |
| 5,590,648 A | | 1/1997 | Mitchell et al. |
| 5,591,216 A | | 1/1997 | Testerman et al. |
| 5,593,431 A | | 1/1997 | Sheldon |
| 5,605,151 A | | 2/1997 | Lynn et al. |
| 5,606,969 A | | 3/1997 | Butler et al. |
| 5,620,466 A | | 4/1997 | Haefner et al. |
| 5,622,178 A | | 4/1997 | Gilham |
| 5,626,622 A | * | 5/1997 | Cooper .......... 607/18 |
| 5,632,281 A | | 5/1997 | Rayburn et al. |

(56) References Cited

U.S. PATENT DOCUMENTS

| | | | |
|---|---|---|---|
| 5,634,938 A | 6/1997 | Swanson et al. | |
| 5,641,326 A | 6/1997 | Adams | |
| 5,643,330 A | 7/1997 | Holsheimer et al. | |
| 5,658,318 A | 8/1997 | Stroetmann et al. | |
| 5,662,688 A | 9/1997 | Haefner et al. | |
| 5,683,430 A | 11/1997 | Markowitz et al. | |
| 5,690,681 A | 11/1997 | Geddes et al. | |
| 5,693,000 A | 12/1997 | Crosby et al. | |
| 5,697,951 A | 12/1997 | Harpstead et al. | |
| 5,697,953 A | 12/1997 | Kroll et al. | |
| 5,700,282 A | 12/1997 | Zabara et al. | |
| 5,701,894 A | 12/1997 | Cherry et al. | |
| 5,704,345 A | 1/1998 | Berthon et al. | |
| 5,704,365 A | 1/1998 | Albrecht et al. | |
| 5,707,400 A | 1/1998 | Terry, Jr. et al. | |
| 5,713,933 A | 2/1998 | Condie et al. | |
| 5,716,377 A | 2/1998 | Rise et al. | |
| 5,720,769 A * | 2/1998 | van Oort et al. | 607/17 |
| 5,720,771 A | 2/1998 | Snell | |
| 5,724,984 A | 3/1998 | Arnold et al. | |
| 5,727,558 A | 3/1998 | Hakki et al. | |
| 5,738,102 A | 4/1998 | Lemelson | |
| 5,766,236 A | 6/1998 | Detty et al. | |
| 5,792,188 A | 8/1998 | Starkweather et al. | |
| 5,794,615 A | 8/1998 | Estes et al. | |
| 5,800,464 A | 9/1998 | Kieval | |
| 5,800,470 A | 9/1998 | Stein et al. | |
| 5,802,188 A | 9/1998 | McDonough | |
| 5,814,087 A * | 9/1998 | Renirie | 607/21 |
| 5,826,579 A | 10/1998 | Remmers et al. | |
| 5,827,326 A | 10/1998 | Kroll et al. | |
| 5,839,430 A | 11/1998 | Cama et al. | |
| 5,861,011 A * | 1/1999 | Stoop | 607/25 |
| 5,861,015 A | 1/1999 | Benja | |
| 5,871,011 A | 2/1999 | Howell et al. | |
| 5,895,414 A | 4/1999 | Sanchez-Zambrano | |
| 5,902,250 A * | 5/1999 | Verrier et al. | 600/515 |
| 5,916,239 A | 6/1999 | Geddes et al. | |
| 5,919,141 A | 7/1999 | Money et al. | |
| 5,919,220 A | 7/1999 | Stieglitz et al. | |
| 5,928,272 A | 7/1999 | Adkins et al. | |
| 5,938,596 A | 8/1999 | Woloszko et al. | |
| 5,944,680 A | 8/1999 | Christopherson et al. | |
| 5,957,861 A | 9/1999 | Combs et al. | |
| 5,957,956 A | 9/1999 | Kroll et al. | |
| 5,961,446 A | 10/1999 | Beller et al. | |
| 5,961,450 A | 10/1999 | Merchant et al. | |
| 5,964,788 A | 10/1999 | Greenhut | |
| 5,970,975 A | 10/1999 | Estes et al. | |
| 5,974,349 A | 10/1999 | Levine et al. | |
| 5,981,011 A | 11/1999 | Overcash et al. | |
| 5,989,230 A | 11/1999 | Frassica | |
| 6,006,134 A | 12/1999 | Hill et al. | |
| 6,015,388 A | 1/2000 | Sackner et al. | |
| 6,016,449 A | 1/2000 | Fischell et al. | |
| 6,021,351 A | 2/2000 | Kadhiresan et al. | |
| 6,044,297 A | 3/2000 | Sheldon et al. | |
| 6,047,203 A | 4/2000 | Sackner et al. | |
| 6,050,940 A | 4/2000 | Braun et al. | |
| 6,050,952 A | 4/2000 | Hakki et al. | |
| 6,058,331 A | 5/2000 | King | |
| 6,059,725 A | 5/2000 | Steinschneider | |
| 6,073,048 A | 6/2000 | Kieval et al. | |
| 6,091,973 A | 7/2000 | Colla et al. | |
| 6,091,986 A | 7/2000 | Keimel | |
| 6,099,479 A | 8/2000 | Christopherson et al. | |
| 6,105,575 A | 8/2000 | Estes et al. | |
| 6,110,098 A | 8/2000 | Renirie et al. | |
| 6,120,441 A | 9/2000 | Griebel et al. | |
| 6,126,611 A | 10/2000 | Bourgeois et al. | |
| 6,128,534 A * | 10/2000 | Park et al. | 607/17 |
| 6,132,384 A | 10/2000 | Christopherson et al. | |
| 6,134,470 A | 10/2000 | Hartlaub et al. | |
| 6,144,866 A | 11/2000 | Miesel et al. | |
| 6,148,230 A | 11/2000 | KenKnight | |
| 6,148,814 A | 11/2000 | Clemmer et al. | |
| 6,155,976 A | 12/2000 | Sackner et al. | |
| 6,161,041 A * | 12/2000 | Stoop et al. | 607/14 |
| 6,161,042 A | 12/2000 | Hartley et al. | |
| 6,161,047 A | 12/2000 | King et al. | |
| 6,168,568 B1 | 1/2001 | Gavriely | |
| 6,178,349 B1 | 1/2001 | Kieval | |
| 6,181,961 B1 | 1/2001 | Prass | |
| 6,181,966 B1 | 1/2001 | Nigam | |
| 6,190,326 B1 | 2/2001 | McKinnon et al. | |
| 6,200,265 B1 | 3/2001 | Walsh et al. | |
| 6,206,914 B1 | 3/2001 | Soykan et al. | |
| 6,208,894 B1 | 3/2001 | Schulman et al. | |
| 6,212,435 B1 | 4/2001 | Lattner et al. | |
| 6,221,011 B1 | 4/2001 | Bardy | |
| 6,236,873 B1 | 5/2001 | Holmström | |
| 6,240,314 B1 | 5/2001 | Plicchi et al. | |
| 6,251,126 B1 | 6/2001 | Ottenhoff et al. | |
| 6,258,039 B1 | 7/2001 | Okamoto et al. | |
| 6,261,238 B1 | 7/2001 | Gavriely | |
| 6,263,244 B1 | 7/2001 | Mann et al. | |
| 6,264,606 B1 | 7/2001 | Ekwall et al. | |
| 6,269,269 B1 | 7/2001 | Ottenhoff et al. | |
| 6,272,377 B1 | 8/2001 | Sweeney et al. | |
| 6,275,733 B1 * | 8/2001 | Park et al. | 607/18 |
| 6,280,462 B1 | 8/2001 | Hauser et al. | |
| 6,286,508 B1 | 9/2001 | Remmers et al. | |
| 6,287,264 B1 | 9/2001 | Hoffman | |
| 6,292,695 B1 | 9/2001 | Webster, Jr. et al. | |
| 6,292,703 B1 | 9/2001 | Meier et al. | |
| 6,303,270 B1 | 10/2001 | Flaim et al. | |
| 6,306,088 B1 | 10/2001 | Krausman et al. | |
| 6,310,085 B1 | 10/2001 | Willis | |
| 6,317,627 B1 | 11/2001 | Ennen et al. | |
| 6,331,536 B1 | 12/2001 | Radulovacki et al. | |
| 6,351,670 B1 | 2/2002 | Kroll | |
| 6,356,788 B2 | 3/2002 | Boveja | |
| 6,357,444 B1 | 3/2002 | Parker | |
| 6,360,127 B1 | 3/2002 | Ding et al. | |
| 6,361,494 B1 | 3/2002 | Lindenthaler | |
| 6,361,522 B1 | 3/2002 | Scheiner et al. | |
| 6,363,270 B1 | 3/2002 | Colla et al. | |
| 6,366,813 B1 | 4/2002 | DiLorenzo | |
| 6,368,287 B1 | 4/2002 | Hadas | |
| 6,375,614 B1 | 4/2002 | Braun et al. | |
| 6,375,621 B1 | 4/2002 | Sullivan | |
| 6,375,623 B1 | 4/2002 | Gavriely | |
| 6,387,907 B1 | 5/2002 | Hendricks et al. | |
| 6,397,109 B1 | 5/2002 | Cammilli et al. | |
| 6,397,845 B1 | 6/2002 | Burton | |
| 6,398,739 B1 | 6/2002 | Sullivan et al. | |
| 6,400,982 B2 | 6/2002 | Sweeney et al. | |
| 6,401,129 B1 | 6/2002 | Lenander | |
| 6,409,675 B1 | 6/2002 | Turcott | |
| 6,409,676 B2 | 6/2002 | Ruton et al. | |
| 6,411,845 B1 | 6/2002 | Mower | |
| 6,411,850 B1 | 6/2002 | Kay et al. | |
| 6,415,174 B1 | 7/2002 | Bebehani et al. | |
| 6,415,183 B1 | 7/2002 | Scheiner et al. | |
| 6,421,557 B1 | 7/2002 | Meyer | |
| 6,431,171 B1 | 8/2002 | Burton | |
| 6,438,407 B1 | 8/2002 | Ousdigian et al. | |
| 6,438,428 B1 | 8/2002 | Axelgaard et al. | |
| 6,442,413 B1 | 8/2002 | Silver | |
| 6,442,435 B2 | 8/2002 | King et al. | |
| 6,447,459 B1 | 9/2002 | Larom | |
| 6,449,507 B1 | 9/2002 | Hill et al. | |
| 6,450,957 B1 | 9/2002 | Yoshimi et al. | |
| 6,454,708 B1 | 9/2002 | Ferguson et al. | |
| 6,454,719 B1 | 9/2002 | Greenhut | |
| 6,463,326 B1 | 10/2002 | Hartley et al. | |
| 6,463,327 B1 | 10/2002 | Lurie et al. | |
| 6,467,333 B2 | 10/2002 | Lewis et al. | |
| 6,468,219 B1 | 10/2002 | Njemanze | |
| 6,473,644 B1 | 10/2002 | Terry, Jr. et al. | |
| 6,487,450 B1 | 11/2002 | Chen | |
| 6,491,639 B1 | 12/2002 | Turcott | |
| 6,493,585 B2 | 12/2002 | Plicchi et al. | |
| 6,497,658 B2 | 12/2002 | Roizen et al. | |

(56) References Cited

U.S. PATENT DOCUMENTS

| | | |
|---|---|---|
| 6,511,500 B1 | 1/2003 | Rahme |
| 6,512,940 B1 | 1/2003 | Brabec et al. |
| 6,514,218 B2 | 2/2003 | Yamamoto |
| 6,517,497 B2 | 2/2003 | Rymut et al. |
| 6,522,915 B1 | 2/2003 | Ceballos et al. |
| 6,522,926 B1 | 2/2003 | Kieval et al. |
| 6,527,729 B1 | 3/2003 | Turcott |
| 6,532,388 B1 | 3/2003 | Hill et al. |
| 6,542,774 B2 | 4/2003 | Hill et al. |
| 6,547,743 B2 | 4/2003 | Brydon |
| 6,564,096 B2 | 5/2003 | Mest |
| 6,564,101 B1 | 5/2003 | Zikria |
| 6,564,106 B2 | 5/2003 | Guck et al. |
| 6,572,543 B1 | 6/2003 | Christopherson et al. |
| 6,572,557 B2 | 6/2003 | Tchou et al. |
| 6,574,507 B1 | 6/2003 | Bonnet |
| 6,580,944 B1 | 6/2003 | Katz et al. |
| 6,589,188 B1 | 7/2003 | Street et al. |
| 6,595,928 B2 | 7/2003 | Mansy et al. |
| 6,600,956 B2 | 7/2003 | Maschino et al. |
| 6,606,993 B1 | 8/2003 | Wiesmann et al. |
| 6,607,509 B2 | 8/2003 | Bobroff et al. |
| 6,611,713 B2 | 8/2003 | Schauerte |
| 6,615,083 B2 | 9/2003 | Küpper |
| 6,622,041 B2 | 9/2003 | Terry, Jr. et al. |
| 6,622,046 B2 | 9/2003 | Fraley et al. |
| 6,628,986 B1 | 9/2003 | Mouchawar et al. |
| 6,628,987 B1 | 9/2003 | Hill et al. |
| 6,641,542 B2 | 11/2003 | Cho et al. |
| 6,658,292 B2 | 12/2003 | Kroll et al. |
| 6,662,032 B1 | 12/2003 | Gavish et al. |
| 6,679,250 B2 | 1/2004 | Walker |
| 6,694,186 B2 | 2/2004 | Bardy |
| 6,704,590 B2 | 3/2004 | Haldeman |
| 6,708,058 B2 | 3/2004 | Kim et al. |
| 6,708,063 B2 | 3/2004 | Czygan et al. |
| 6,723,055 B2 | 4/2004 | Hoffman |
| 6,731,984 B2 * | 5/2004 | Cho et al. ................ 607/17 |
| 6,741,885 B1 | 5/2004 | Park et al. |
| 6,748,252 B2 | 6/2004 | Lynn et al. |
| 6,752,765 B1 | 6/2004 | Jensen et al. |
| 6,752,766 B2 | 6/2004 | Kowallik et al. |
| 6,765,062 B2 | 7/2004 | Chin et al. |
| 6,770,022 B2 | 8/2004 | Mechlenburg et al. |
| 6,770,029 B2 | 8/2004 | Iliff |
| 6,773,404 B2 | 8/2004 | Poezevera et al. |
| 6,786,866 B2 | 9/2004 | Odagiri et al. |
| 6,810,287 B2 | 10/2004 | Zhu et al. |
| 6,832,609 B2 | 12/2004 | Wright et al. |
| 6,881,192 B1 | 4/2005 | Park |
| 6,892,095 B2 | 5/2005 | Salo |
| 6,894,204 B2 | 5/2005 | Dunshee |
| 6,895,275 B2 | 5/2005 | Markowitz et al. |
| 6,904,320 B2 | 6/2005 | Park et al. |
| 6,907,288 B2 | 6/2005 | Daum |
| 6,910,481 B2 | 6/2005 | Kimmel et al. |
| 6,928,324 B2 | 8/2005 | Park et al. |
| 6,932,084 B2 | 8/2005 | Estes et al. |
| 6,934,583 B2 | 8/2005 | Weinberg et al. |
| 6,942,686 B1 | 9/2005 | Barbut et al. |
| 6,951,539 B2 | 10/2005 | Bardy |
| 6,964,641 B2 | 11/2005 | Cho et al. |
| 6,975,903 B1 * | 12/2005 | Min et al. ................ 607/24 |
| 6,988,498 B2 | 1/2006 | Berthon-Jones et al. |
| 6,999,817 B2 | 2/2006 | Park et al. |
| 7,010,337 B2 | 3/2006 | Furnary et al. |
| 7,025,729 B2 | 4/2006 | de Chazal et al. |
| 7,039,468 B2 | 5/2006 | Freed et al. |
| 7,062,308 B1 | 6/2006 | Jackson |
| 7,065,409 B2 | 6/2006 | Mazar |
| 7,089,936 B2 | 8/2006 | Madaus et al. |
| 7,092,755 B2 | 8/2006 | Florio |
| 7,101,341 B2 | 9/2006 | Tsukashima et al. |
| 7,117,036 B2 | 10/2006 | Florio |
| 7,127,300 B2 | 10/2006 | Mazar et al. |
| 7,130,687 B2 | 10/2006 | Cho et al. |
| 7,136,704 B2 | 11/2006 | Schulman |
| 7,155,278 B2 | 12/2006 | King et al. |
| 7,155,284 B1 | 12/2006 | Whitehurst et al. |
| 7,168,429 B2 | 1/2007 | Matthews et al. |
| 7,184,817 B2 | 2/2007 | Zhu et al. |
| 7,189,204 B2 | 3/2007 | Ni et al. |
| 7,194,313 B2 | 3/2007 | Libbus |
| 7,204,805 B2 | 4/2007 | Dean |
| 7,206,635 B2 | 4/2007 | Cho et al. |
| 7,207,945 B2 | 4/2007 | Bardy |
| 7,212,862 B2 | 5/2007 | Park et al |
| 7,218,964 B2 | 5/2007 | Hill et al. |
| 7,225,013 B2 | 5/2007 | Geva et al. |
| 7,225,809 B1 | 6/2007 | Bowen et al. |
| 7,231,250 B2 | 6/2007 | Band et al. |
| 7,245,971 B2 | 7/2007 | Park |
| 7,252,640 B2 | 8/2007 | Ni et al. |
| 7,258,670 B2 | 8/2007 | Bardy |
| 7,269,459 B1 | 9/2007 | Koh |
| 7,277,757 B2 | 10/2007 | Casavant et al. |
| 7,277,761 B2 | 10/2007 | Shelchuk |
| 7,302,295 B2 | 11/2007 | Stahmann et al. |
| 7,314,046 B2 | 1/2008 | Schroeder et al. |
| 7,366,572 B2 | 4/2008 | Heruth et al. |
| 7,376,463 B2 | 5/2008 | Salo et al. |
| 7,396,333 B2 | 7/2008 | Stahmann et al. |
| 7,400,928 B2 | 7/2008 | Hatlestsad |
| 7,413,549 B1 | 8/2008 | Koh |
| 7,425,200 B2 | 9/2008 | Brockway et al. |
| 7,428,468 B2 | 9/2008 | Takemura et al. |
| 7,435,221 B1 | 10/2008 | Bharmi et al. |
| 7,440,795 B2 | 10/2008 | Poezevara |
| 7,460,906 B2 | 12/2008 | Libbus |
| 7,469,697 B2 | 12/2008 | Lee et al. |
| 7,486,991 B2 | 2/2009 | Libbus et al. |
| 7,499,742 B2 | 3/2009 | Bolea et al. |
| 7,509,164 B2 | 3/2009 | Jensen et al. |
| 7,509,166 B2 | 3/2009 | Libbus |
| 7,680,537 B2 | 3/2010 | Stahmann et al. |
| 7,720,541 B2 | 5/2010 | Stahmann et al. |
| 7,766,842 B2 | 8/2010 | Ni et al. |
| 8,192,376 B2 | 6/2012 | Lovett et al. |
| 2001/0031930 A1 | 10/2001 | Roizen et al. |
| 2002/0005982 A1 | 1/2002 | Borlinghaus |
| 2002/0026222 A1 | 2/2002 | Schauerte et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0058877 A1 | 5/2002 | Baumann et al. |
| 2002/0068897 A1 | 6/2002 | Jenkins et al. |
| 2002/0068958 A1 | 6/2002 | Bardy et al. |
| 2002/0072773 A1 | 6/2002 | Bardy et al. |
| 2002/0072776 A1 | 6/2002 | Osorio et al. |
| 2002/0082652 A1 | 6/2002 | Wentkowski et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0103516 A1 | 8/2002 | Patwardhan et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107553 A1 | 8/2002 | Hill et al. |
| 2002/0107559 A1 | 8/2002 | Sanders et al. |
| 2002/0120299 A1 | 8/2002 | Ostroff et al. |
| 2002/0128700 A1 | 9/2002 | Cross, Jr. |

(56) References Cited

U.S. PATENT DOCUMENTS

| | | |
|---|---|---|
| 2002/0143264 A1 | 10/2002 | Ding et al. |
| 2002/0143369 A1 | 10/2002 | Hill et al. |
| 2002/0151051 A1 | 10/2002 | Li |
| 2002/0161410 A1 | 10/2002 | Kramer et al. |
| 2002/0165462 A1 | 11/2002 | Westbrook et al. |
| 2002/0169384 A1 | 11/2002 | Kowallik et al. |
| 2002/0169485 A1 | 11/2002 | Pless et al. |
| 2002/0183237 A1 | 12/2002 | Puskas |
| 2002/0193685 A1 | 12/2002 | Mate et al. |
| 2002/0193697 A1* | 12/2002 | Cho et al. ............ 600/529 |
| 2002/0193839 A1* | 12/2002 | Cho et al. ............ 607/17 |
| 2002/0198570 A1 | 12/2002 | Puskas |
| 2003/0003052 A1 | 1/2003 | Hampton |
| 2003/0004546 A1 | 1/2003 | Casey |
| 2003/0004549 A1 | 1/2003 | Hill et al. |
| 2003/0004552 A1 | 1/2003 | Plombon |
| 2003/0023175 A1 | 1/2003 | Arzbaecher et al. |
| 2003/0023279 A1 | 1/2003 | Spinelli |
| 2003/0036773 A1 | 2/2003 | Whitehurst et al. |
| 2003/0036778 A1 | 2/2003 | Ostroff et al. |
| 2003/0045904 A1 | 3/2003 | Bardy et al. |
| 2003/0045909 A1 | 3/2003 | Gross et al. |
| 2003/0045914 A1 | 3/2003 | Cohen et al. |
| 2003/0050538 A1 | 3/2003 | Naghavi et al. |
| 2003/0055461 A1 | 3/2003 | Girouard et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0069609 A1 | 4/2003 | Thompson |
| 2003/0073919 A1 | 4/2003 | Hampton et al. |
| 2003/0074039 A1 | 4/2003 | Puskas |
| 2003/0078629 A1 | 4/2003 | Chen |
| 2003/0083241 A1 | 5/2003 | Young |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0100924 A1 | 5/2003 | Foreman et al. |
| 2003/0105493 A1 | 6/2003 | Salo |
| 2003/0111079 A1 | 6/2003 | Matthews et al. |
| 2003/0149450 A1 | 8/2003 | Mayberg |
| 2003/0153955 A1 | 8/2003 | Park et al. |
| 2003/0153956 A1 | 8/2003 | Park et al. |
| 2003/0171687 A1 | 9/2003 | Irie et al. |
| 2003/0171791 A1 | 9/2003 | KenKnight et al. |
| 2003/0178031 A1 | 9/2003 | Du Pen et al. |
| 2003/0181951 A1 | 9/2003 | Cates |
| 2003/0187336 A1 | 10/2003 | Odagiri et al. |
| 2003/0195571 A1 | 10/2003 | Burnes et al. |
| 2003/0195578 A1 | 10/2003 | Perron et al. |
| 2003/0199945 A1 | 10/2003 | Ciulla |
| 2003/0204213 A1* | 10/2003 | Jensen et al. ............ 607/17 |
| 2003/0212436 A1 | 11/2003 | Brown |
| 2003/0212440 A1 | 11/2003 | Boveja |
| 2003/0216789 A1 | 11/2003 | Deem et al. |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0002742 A1 | 1/2004 | Florio |
| 2004/0019364 A1 | 1/2004 | Kieval et al. |
| 2004/0059240 A1 | 3/2004 | Cho et al. |
| 2004/0073093 A1 | 4/2004 | Hatlestad |
| 2004/0102814 A1 | 5/2004 | Sorensen et al. |
| 2004/0116981 A1 | 6/2004 | Mazar |
| 2004/0122487 A1 | 6/2004 | Hatlestad et al. |
| 2004/0122488 A1 | 6/2004 | Mazar |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0172074 A1 | 9/2004 | Yoshihito |
| 2004/0176809 A1 | 9/2004 | Cho et al. |
| 2004/0193231 A1 | 9/2004 | David et al. |
| 2004/0210154 A1 | 10/2004 | Kline |
| 2004/0210155 A1 | 10/2004 | Takemura et al. |
| 2004/0210261 A1 | 10/2004 | King et al. |
| 2004/0215240 A1 | 10/2004 | Lovett et al. |
| 2004/0215289 A1 | 10/2004 | Fukui |
| 2004/0230229 A1 | 11/2004 | Lovett et al. |
| 2004/0230230 A1 | 11/2004 | Lindstrom et al. |
| 2004/0249299 A1 | 12/2004 | Cobb |
| 2004/0249416 A1 | 12/2004 | Yun et al. |
| 2004/0254616 A1 | 12/2004 | Rossing et al. |
| 2005/0004615 A1 | 1/2005 | Sanders |
| 2005/0021092 A1 | 1/2005 | Yun et al. |
| 2005/0039745 A1 | 2/2005 | Stahmann et al. |
| 2005/0042589 A1 | 2/2005 | Hatlestad et al. |
| 2005/0043772 A1 | 2/2005 | Stahmann et al. |
| 2005/0065447 A1 | 3/2005 | Lee et al. |
| 2005/0065567 A1 | 3/2005 | Lee et al. |
| 2005/0065572 A1 | 3/2005 | Hartley et al. |
| 2005/0065575 A1 | 3/2005 | Dobak |
| 2005/0076908 A1 | 4/2005 | Lee et al. |
| 2005/0085864 A1 | 4/2005 | Schulman et al. |
| 2005/0093581 A1 | 5/2005 | Kang |
| 2005/0096705 A1 | 5/2005 | Pastore et al. |
| 2005/0101841 A9 | 5/2005 | Kaylor et al. |
| 2005/0107838 A1 | 5/2005 | Lovett et al. |
| 2005/0119711 A1 | 6/2005 | Cho et al. |
| 2005/0131467 A1 | 6/2005 | Boveja |
| 2005/0137645 A1 | 6/2005 | Voipio et al. |
| 2005/0142070 A1 | 6/2005 | Hartley et al. |
| 2005/0143779 A1 | 6/2005 | Libbus |
| 2005/0143787 A1 | 6/2005 | Boveja et al. |
| 2005/0145246 A1 | 7/2005 | Hartley et al. |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Scheiner et al. |
| 2005/0149156 A1 | 7/2005 | Libbus et al. |
| 2005/0159784 A1 | 7/2005 | Arceta |
| 2005/0197675 A1 | 9/2005 | David et al. |
| 2005/0288728 A1 | 12/2005 | Libbus et al. |
| 2006/0047333 A1 | 3/2006 | Tockman |
| 2006/0079802 A1 | 4/2006 | Jensen et al. |
| 2006/0079945 A1 | 4/2006 | Libbus |
| 2006/0106428 A1 | 5/2006 | Libbus et al. |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0195041 A1 | 8/2006 | Lynn et al. |
| 2006/0206153 A1 | 9/2006 | Libbus et al. |
| 2006/0206154 A1 | 9/2006 | Moffitt et al. |
| 2006/0217772 A1 | 9/2006 | Libbus et al. |
| 2006/0224188 A1 | 10/2006 | Libbus et al. |
| 2006/0293714 A1 | 12/2006 | Salo et al. |
| 2007/0038278 A1 | 2/2007 | Zarembo |
| 2007/0055115 A1 | 3/2007 | Kwok et al. |
| 2007/0093875 A1 | 4/2007 | Chavan et al. |
| 2007/0112388 A1 | 5/2007 | Salo |
| 2007/0142871 A1 | 6/2007 | Libbus et al. |
| 2007/0149860 A1 | 6/2007 | Lynn et al. |
| 2007/0150014 A1 | 6/2007 | Kramer et al. |
| 2007/0161873 A1 | 7/2007 | Ni et al. |
| 2007/0185542 A1 | 8/2007 | Bolea et al. |
| 2007/0282215 A1 | 12/2007 | Ni et al. |
| 2008/0045813 A1 | 2/2008 | Phuah et al. |
| 2009/0007918 A1 | 1/2009 | Darkin et al. |

FOREIGN PATENT DOCUMENTS

| | | |
|---|---|---|
| EP | 1163877 A1 * | 12/2001 |
| EP | 1317943 B1 | 3/2005 |
| EP | 1151718 B1 | 1/2007 |

(56) References Cited

FOREIGN PATENT DOCUMENTS

| JP | 2002519161 A | 7/2002 |
|---|---|---|
| WO | 2004062485 A2 | 7/2004 |
| WO | 2005028029 A2 | 3/2005 |

OTHER PUBLICATIONS

S. Andreas, et al. "Changes in heart rate during obstructive sleep apnoea"; Eur. Respir. J. 1992, 5,853-857.*

Pitzalis, M. V. et al.; "Effect of respiratory rate on the relationships between RR interval and systolic blood pressure fluctuations: a frequency-dependent phenomenon"; Cardiovascular Research 38 (1998) 332-339.*

Snyder, F. et al.; "Changes in respiration, heart rate, and systolic blood pressure in human sleep"; J. Appl. Physiol. 1964 Mat; 19417-22.*

2001, Balaban et al., Feasibility of Screening for Sleep Apnea Using Pacemaker Impedance Sensor, NASPE 22nd Annual Scientific Sessions, Apr. 2001, vol. 24, No. 4, Part II, #313, 1 page, Abstract Only.

Ajilore et al., Nightcap: Laboratory and home-based evaluation of a portable sleep monitor, 32 Psychophysiology, 32-98 (1995). Abstract only.

Garrigue et al., Night Atrial Overdrive with DDD Pacing Results in a Significant Reduction of Sleep Apnea Episodes and QOL Improvement in Heart Failure Patients, NASPE, 2001, 1 page, #145, Abstract Only.

Hilton et al., "Evaluation of Frequency and Time-frequency Spectral Analysis of Heart Rate Variability as a Diagnostic Marker of the Sleep Apnea Syndrome." Med Biol Eng Comput Nov. 1999, 37(6), 760-9.

* cited by examiner

SLEEP DETECTION USING AN ADJUSTABLE THRESHOLD

RELATED PATENT DOCUMENTS

This is a continuation of U.S. patent application Ser. No. 11/717,561, filed on Mar. 13, 2007, which is a divisional of U.S. patent application Ser. No. 10/309,771, filed on Dec. 4, 2002, issued as U.S. Pat. No. 7,189,204 on Mar. 13, 2007, to which Applicant claims priority under 35 U.S.C. §120, and which is incorporated herein by reference.

FIELD OF THE INVENTION

The present invention relates generally to sleep detection and, more particularly, to detecting sleep by adjusting a sleep threshold associated with a first sleep-related signal using a second sleep-related signal.

BACKGROUND OF THE INVENTION

Sleep is generally beneficial and restorative to a patient, exerting great influence on the quality of life. A typical night's sleep for a normal person begins with a sleep stage known as slow wave sleep (SWS) characterized by low frequency electroencephalogram (EEG) activity. As the person falls asleep, brain activity declines and there is a progressive increase in the depth of sleep. At approximately ninety minute intervals, sleep lightens and a sleep stage known as rapid eye movement (REM) sleep is initiated. REM sleep is characterized by high frequency EEG activity, bursts of rapid eye movements, skeletal muscle atonia, and heightened autonomic activity.

There are typically 4-6 REM periods per night, with increasing duration and intensity toward morning. While dreams can occur during either REM or SWS sleep, the nature of the dreams varies depending on the type of sleep. REM sleep dreams tend to be more vivid and emotionally intense than SWS sleep dreams. Furthermore, autonomic nervous system activity is dramatically altered when REM sleep is initiated.

In patients with respiratory or heart disease, the brain during sleep can precipitate breathing disturbances, myocardial ischemia, or arrhythmia. Although REM sleep is a necessary component of normal sleep, serious consequences may be associated with both the increase in autonomic activity and the intense emotional responses that accompany dreaming in patients with cardiovascular disease or respiratory disorders, for example.

Disruptions of the respiratory system during sleep may include the conditions of sleep apnea or sleep hypopnea. Sleep apnea is a serious breathing disorder caused by airway obstruction, denoted obstructive sleep apnea, or derangement in central nervous system control of respiration, denoted central sleep apnea. Regardless of the type of apnea, people with sleep apnea stop breathing repeatedly during their sleep, sometimes hundreds of times a night and often for a minute or longer. Whereas sleep apnea refers to cessation of breathing, hypopnea is associated with periods of abnormally slow or shallow breathing. With each apnea or hypopnea event, the person generally briefly arouses to resume normal breathing. As a result, people with sleep apnea or hypopnea may experience sleep fragmented by frequent arousals.

An adequate quality and quantity of sleep is required to maintain physiological homeostasis. Prolonged sleep deprivation or periods of highly fragmented sleep ultimately will have serious health consequences. Chronic lack of sleep may be associated with various cardiac or respiratory disorders affecting a patient's health and quality of life.

SUMMARY OF THE INVENTION

The present invention is directed to detecting sleep. In one embodiment of the invention, a device for detecting sleep includes a first sensor for sensing a first sleep-related signal and a second sensor for sensing a second sleep-related signal, wherein the first and the second sleep-related signals are indicative of sleep. A sleep detector coupled to the first and the second sensors is configured to adjust a sleep threshold associated with the first sleep-related signal using the second sleep-related signal. The sleep detector detects a sleep condition by comparing the first sleep-related signal with the adjusted threshold. A component of one or more of the sleep detector, first sensor, and second sensor is implantable.

In accordance with another embodiment of the present invention, a method for sleep detection involves adjusting a sleep threshold associated with a first sleep-related signal using a second sleep-related signal. The first sleep-related signal is compared to the adjusted threshold and sleep is detected based on the comparison.

Yet another embodiment of the invention includes means for adjusting a sleep threshold of a first sleep-related signal using a second sleep-related signal, means for comparing the first sleep-related signal to the adjusted threshold, and means for detecting sleep based on the comparison.

In a further embodiment of the invention, a method for detecting sleep includes sensing a plurality of sleep-related signals. A relationship is defined between at least two of the sleep-related signals, the relationship associated with sleep detection. Sleep is detected using the sleep-related signal relationship. At least one of the sensing and detecting is performed at least in part implantably.

The above summary of the invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
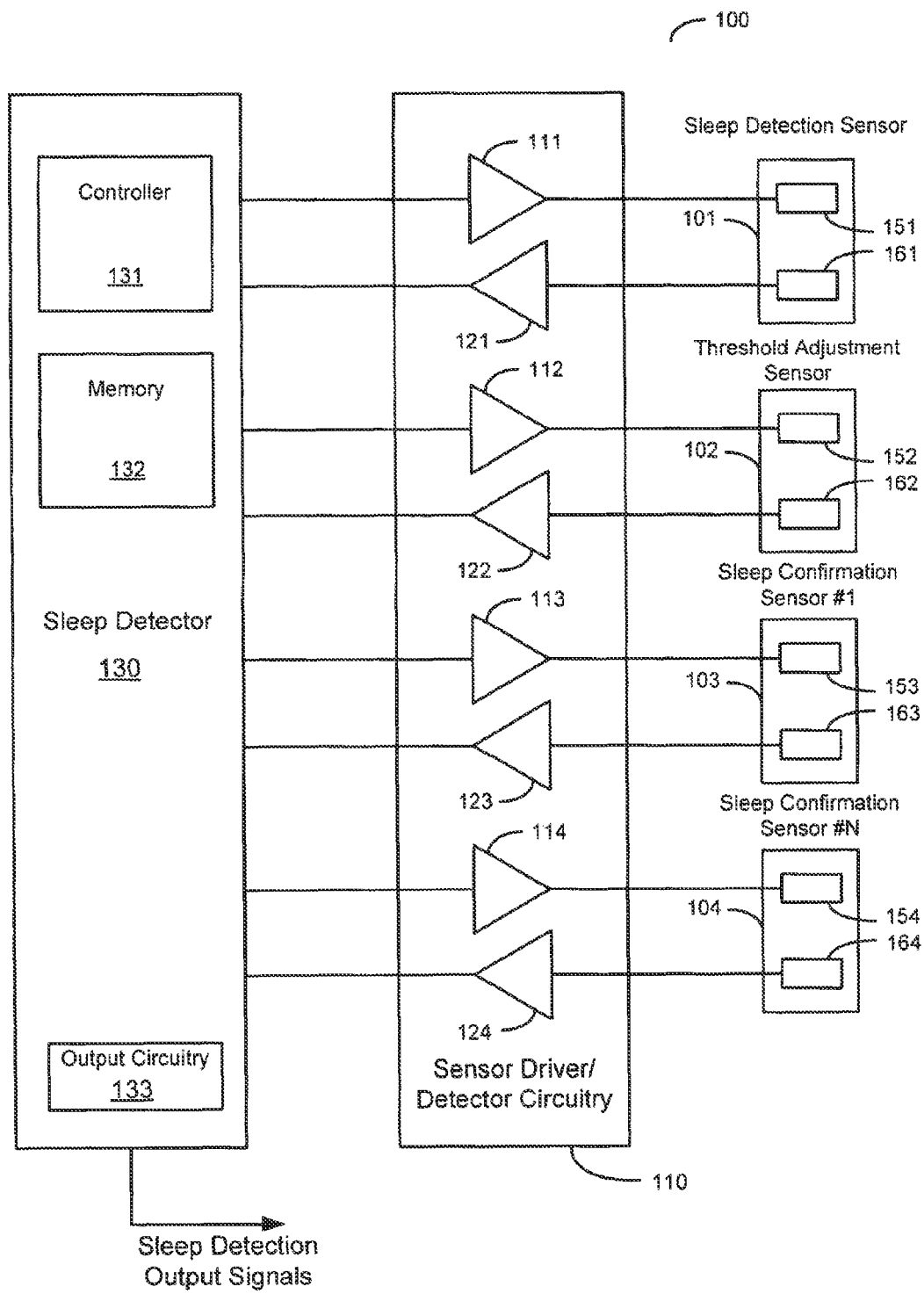
FIG. 1 is a block diagram of a sleep detection device in accordance with an embodiment of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

An adequate duration and quality of sleep is required to maintain sleep-related homeostasis. Prolonged sleep deprivation or periods of poor quality sleep ultimately will have serious health consequences. To diagnose the reasons for sleep disturbances, people suffering from sleep disorders may spend one or more nights in a sleep laboratory. In a sleep laboratory, a patient is typically instrumented for data acquisition and observed by trained personnel. Sleep assessment in a laboratory setting presents a number of obstacles in acquiring an accurate picture of a patient's typical sleep patterns. For example, spending a night in a sleep laboratory typically causes a patient to experience a condition known as "first night syndrome," involving disrupted sleep during the first few nights in an unfamiliar location. Furthermore, sleeping while instrumented and observed may not result in a realistic perspective of the patient's normal sleep patterns.

Sleep quality assessments depend upon acquiring data regarding a patient's typical sleep patterns. An initial step to sleep quality assessment is an accurate and reliable method for recognizing that a patient is asleep. Detecting the onset, termination, duration, stages, and quality of sleep experienced by a patient may be used in connection with the treatment of various conditions. For example, detection of disordered breathing during sleep may be helpful in delivering appropriate therapy for patients suffering from sleep disorders ranging from snoring to sleep apnea. Furthermore, trending sleep data over a long term, including number and severity of disordered breathing episodes, arousal episodes or periods of disturbed sleep, may provide insight into the emotional and physical health of a patient. For example, knowledge of sleep patterns may influence a number of aspects of patient therapy including cardiac or respiratory therapy.

In the context of cardiac rhythm management (CRM) therapy, for example, it may be advantageous to regulate the lower rate limit of a pacemaker based on recognition of sleep or non-sleep states. Adjustment of the lower rate limit to accommodate periods of sleep may improve the quality of the patient's sleep in addition to lengthening battery life of the CRM device. Furthermore, arrhythmia therapy may be improved with sleep recognition. The periods of arousal from REM sleep have been associated with an increased likelihood of arrhythmia for patients with heart disease. Therefore, the ability to recognize sleep may enhance the ability to predict and detect arrhythmias associated with sleep and to provide anti-arrhythmia therapy during sleep.

Respiratory therapy may also be enhanced by a method for accurately recognizing a sleep state. Sleep apnea treatments may include positive airway pressure devices that supply a steady or adjustable flow of air to the patient during sleep, periodic electrical stimulation of the hypoglossal nerve to open the upper airways, and cardiac atrial overdrive pacing to suppress sleep apnea events or awaken the patient to terminate an apneic event. Each of these methods, as well as methods for treating respiratory disorders, may be improved by reliable detection that the patient is sleeping.

Various embodiments of the invention involve detecting sleep using signals associated with a condition of sleep. One embodiment of the invention involves adjusting a sleep threshold associated with a first sleep-related signal using a second sleep-related signal. The first sleep-related signal is compared to the adjusted threshold and sleep is detected based on the comparison. At least one of sensing the sleep-related signals, comparing the first sleep-related signal to the sleep threshold, and detecting sleep is performed at least in part implantably.

Another embodiment of the invention involves defining a relationship between two or more sleep-related signals. The relationship is associated with sleep detection. Sleep is detected using the relationship. Sensing the sleep-related signals and/or detecting sleep is performed at least in part implantably.

Defining a relationship includes, for example, establishing a sleep criterion associated with at least one of the sleep-related signals. The criterion may be, for example, a threshold or other index related to the condition of sleep. Detection of sleep involves comparing the sleep criterion to the state of one or more of the sleep-related signals.

According to one embodiment of the invention, the sleep-related signals may be derived from external or implantable sensors and analyzed by an external sleep detector. Some or all of the sensors may have remote communication capabilities, such as a wireless Bluetooth communications transmitter or transceiver, to link them to the sleep detector.

According to another embodiment of the invention, the sleep-related signals may be derived from external or implantable sensors and analyzed by an implantable device. The sleep detector may be a component of a device that also performs other functions, such as cardiac pacemaker or defibrillation functions. Some or all of the sensors may be wirelessly coupled to the implantable device by telemetry, for example.

According to an embodiment of the present system, methods of sleep detection may be implemented in an implantable cardiac rhythm management (CRM) system configured as a dual chamber pacemaker device which may operate in numerous pacing modes known in the art. The systems and methods of the present invention may also be implemented in various types of implantable or external diagnostic medical devices including, for example, polysomnography devices, respiratory monitors, and cardiac monitors. In addition, the systems and methods of the present invention may be implemented in a number of implantable or external therapeutic medical devices such as continuous positive airway pressure (CPAP) devices or hypoglossal nerve stimulators.

FIG. 1 is a block diagram of a sleep detection device 100 that may be used to detect sleep in accordance with an embodiment of the invention. The sleep detection device includes a number of sensors 101, 102, 103, 104 that sense sleep-related signals associated with sleep. A representative set of sensed sleep-related signals associated with sleep include body movement, heart rate, QT interval, eye movement, respiration rate, transthoracic impedance, tidal volume, minute ventilation, body posture, electroencephalogram (EEG), electrocardiogram (ECG), electrooculogram (EOG), electromyogram (EMG), muscle tone, body temperature, time of day, historical sleep times, blood pressure, and pulse oximetry.

A first sleep-related signal derived from a sleep detection sensor 101 is a signal associated with sleep that is compared to a sleep threshold for detecting the onset and termination of sleep. A second sleep-related signal derived from a threshold adjustment sensor 102 is used to adjust the sleep threshold. Although one sleep detection sensor and one threshold adjustment sensor are shown in FIG. 1, any number of thresholds or other indices corresponding to a number of sleep detection sensors may be used. Furthermore, signals from any number of adjustment sensors may be used to adjust the thresholds or indices of a plurality of sleep detection signals. Additional sleep-related signals derived from confirmation sensors 103, 104 may optionally be used to confirm the onset or termination of the sleep condition.

The sleep-related signals derived from the sensors 101, 102, 103, 104 are received by a sensor driver/detector system 110 which includes detection circuitry 121, 122, 123, 124. The detection circuitry 121, 122, 123, 124 may include, for example, amplifiers, signal processing circuitry, and/or A/D conversion circuitry for each sensor signal. The sensor driver/detector system 110 may further include sensor drive circuitry 111, 112, 113, 114 required to activate the sensors 101, 102, 103, 104.

A sleep detector 130, according to certain embodiments, transmits control signals to the drive circuitry 111, 112, 113, 114 and receives signals from the detection circuitry 121, 122, 123, 124. The sleep detector 130 may include a microprocessor controller 131 which cooperates with memory circuitry 132 for implementing sleep detection methods of the present invention. The memory circuitry 132 may be used to store program data to implement sleep detection, to store parameters associated with sleep detection, such as a sleep threshold, or to store historical data regarding sleep onset and termination over a selected period.

The sleep detector 130 is configured to compare the level of a first sleep-related signal to a sleep threshold adjusted by a second sleep-related signal and determine sleep onset or termination based on the comparison. The sleep detector 130 may use one or more thresholds or indices associated with one or more sleep-related signals. In addition, the sleep detector 130 may use one or more sleep-related signals to adjust the sleep thresholds or indices. Furthermore, the sleep detector 130 may confirm the onset or termination of sleep using an additional number of sleep-related signals.

The sleep detector 130 may include output circuitry 133 for communicating various signals associated with sleep to another device, to other components of a sleep detection device, a data storage device and/or a display device. The signals associated with sleep may include, for example, a sleep detection signal, parameters associated with sleep detection, such as a sleep threshold, and/or historical data relevant to sleep (e.g., historical sleep time data or an average of same which can be used to establish a sleep threshold). The sleep detector may communicate with another device over a wired or wireless communication channel, for example.

The sensors 101, 102, 103, 104 may comprise implantable sensors or external sensors. In one embodiment, the sensors 101, 102, 103, 104 are coupled to the sensor driver/detector circuitry 110 and thus to the sleep detector 130 through a wired connection. In another embodiment, the sensors 101, 102, 103, 104 and sensor driver/detector circuitry 110 are incorporated into sensing devices that include wireless communication capabilities, e.g., a Bluetooth transmitter or transceiver, and may be coupled to the sleep detector 130 through a wireless link. The sleep detector 130 and/or sensor driver/detector circuitry 110 may be incorporated into an implantable or external device.

Figure 2:
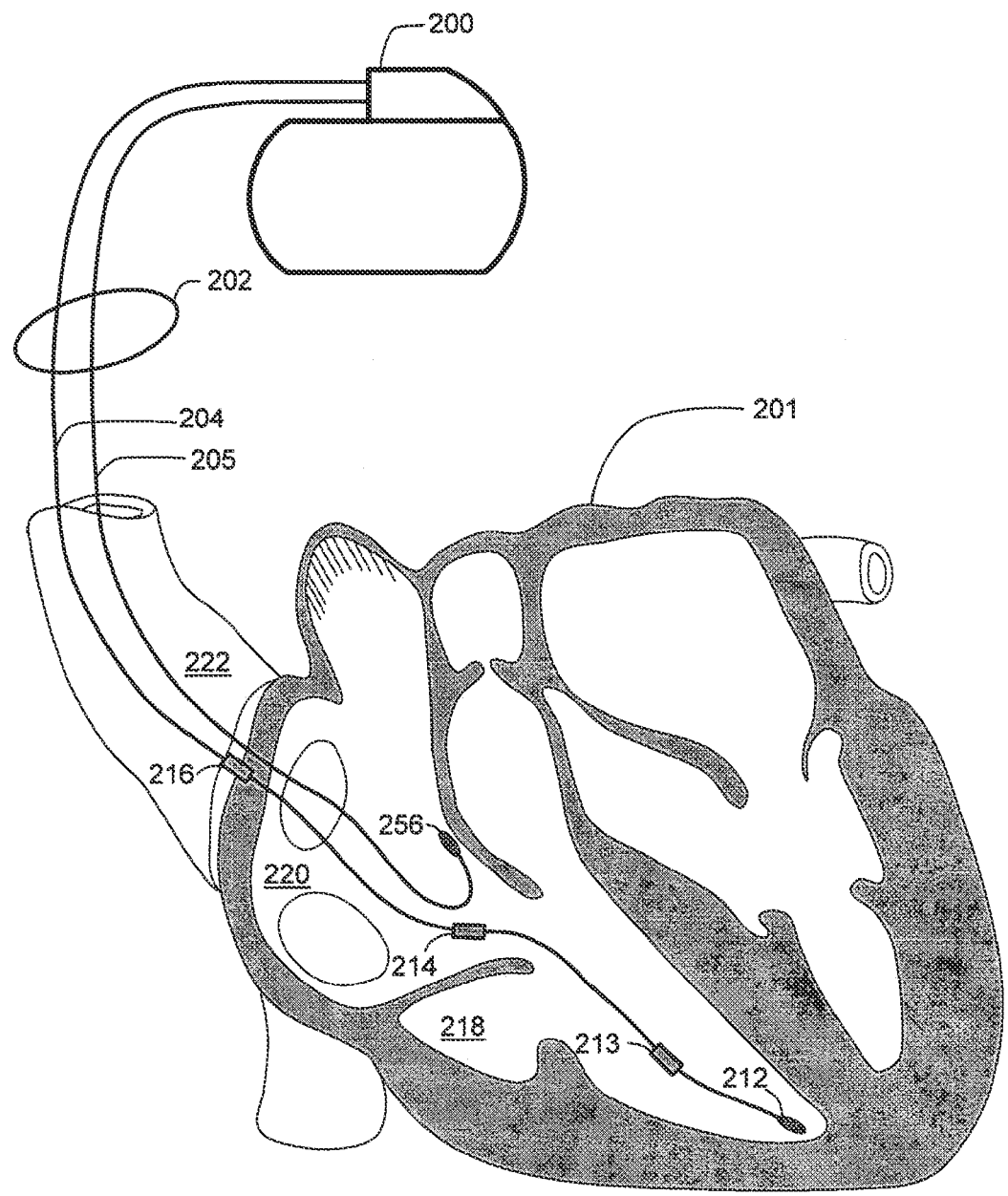
FIG. 2 is a partial view of one embodiment of an implantable medical device that may be used for sleep detection in accordance with an embodiment of the invention.

FIG. 2 is a partial view of one embodiment of an implantable medical device that may be used for sleep detection in accordance with the principles of the invention. The implantable device illustrated in FIG. 2 is a cardiac rhythm management (CRM) system that includes an implantable pacemaker 200 electrically and physically coupled to an intracardiac lead system 202. The intracardiac lead system 202 is implanted in a human body with portions of the intracardiac lead system 202 inserted into a heart 201. The intracardiac lead system 202 is used to detect and analyze electric cardiac signals produced by the heart 201 and to provide electrical energy to the heart 201 under predetermined conditions to treat cardiac arrhythmias of the heart 201.

The CRM 200 depicted in FIG. 2 is a dual chamber device, capable of sensing signals from the right atrium and right ventricle and providing pacing pulses to the right atrium and the right ventricle. Low energy pacing pulses may be delivered to the heart to regulate the heart beat or maintain a lower rate heart beat, for example. In a configuration that includes cardioversion/defibrillation capabilities, high energy pulses may also be delivered to the heart if an arrhythmia is detected that requires cardioversion or defibrillation.

The intracardiac lead system 202 includes a right ventricular lead system 204 and a right atrial lead system 205. The right ventricular lead system 204 includes an RV-tip pace/sense electrode 212 and one or more electrodes 213, 214, 216 suitable for measuring transthoracic impedance. In one arrangement, impedance sense and drive electrodes 216, 214, 213 are configured as ring electrodes. The impedance drive electrode 213 may be located, for example, in the right ventricle 218. The impedance sense electrode 214 may be located in the right atrium 220. Alternatively or additionally, an impedance sense electrode 216 may be located in the superior right atrium 220 or near the right atrium 220 within the superior vena cava 222.

A two-electrode impedance sensing configuration is also possible, wherein the right ventricular lead system includes an impedance drive electrode 213 and a tip electrode 212. In this configuration, the tip electrode 212 may be used as the impedance sense electrode as well as a cardiac sense/pace electrode. Other locations and combinations of impedance sense and drive electrodes are also possible.

The atrial lead system 205 includes an A-tip cardiac pace/sense electrode 256.

In the configuration of FIG. 2, the intracardiac lead system 202 is positioned within the heart 201, with a portion of the atrial lead system 205 extending into the right atrium 220 and portions of the right ventricular lead system 204 extending through the right atrium 220 into the right ventricle 218. The A-tip electrode 256 is positioned at an appropriate location within the right atrium 220 for pacing the right atrium 220 and sensing cardiac activity in the right atrium 220. The RV-tip electrode 212 is positioned at appropriate locations within the right ventricle 218 for pacing the right ventricle 218 and sensing cardiac activity in the right ventricle 218.

Additional configurations of sensing, pacing and defibrillation electrodes can be included in the intracardiac lead system to allow for various sensing, pacing, and defibrillation capabilities of multiple heart chambers. In one configuration, the right ventricular and right atrial leads may include additional electrodes for bipolar sensing and/or pacing, for example. Further, the right ventricular and right atrial leads may also include additional electrodes for cardioversion or defibrillation.

In other configurations, the intracardiac lead system may have only a single lead with electrodes positioned in the right atrium or the right ventricle to implement sleep detection and single chamber cardiac pacing. In yet other embodiments, the intracardiac lead system may include endocardial leads that are advanced into the coronary sinus and coronary veins to locate the distal electrode(s) adjacent to the left ventricle or the left atrium.

Other intracardiac lead and electrode arrangements and configurations known in the art are also possible and considered to be within the scope of the present system.

Figure 3:
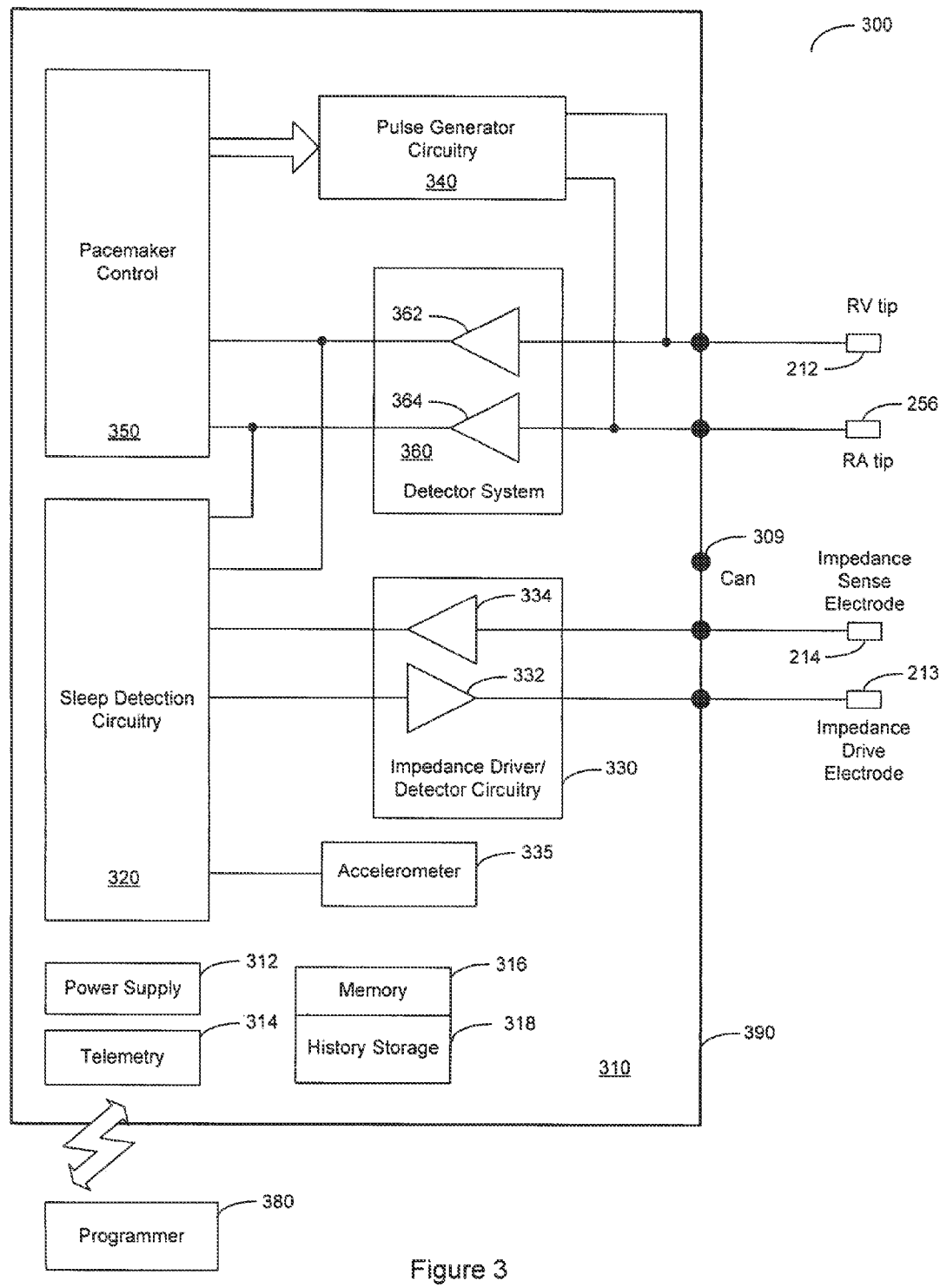
FIG. 3 is a system block diagram of an implantable medical device with which sleep detection may be implemented in accordance with an embodiment of the invention.

Referring now to FIG. 3, there is shown a block diagram of an embodiment of a CRM system 300 configured as a pacemaker and suitable for implementing a sleep detection methodology of the present invention. FIG. 3 shows the CRM 300 divided into functional blocks. It will be understood by those skilled in the art that there exist many possible configurations in which these functional blocks can be arranged and implemented. The example depicted in FIG. 3 is one possible functional arrangement. The CRM 300 includes sleep detection circuitry 320 for receiving sleep-related signals and detecting sleep in accordance with an embodiment of the invention.

In one embodiment, sleep detection circuitry 320 is incorporated as part of the CRM circuitry 310 encased and hermetically sealed in a housing 390 suitable for implanting in a human body. Power to the CRM 300 is supplied by an electrochemical battery power supply 312 housed within the CRM 300. A connector block (not shown) is additionally attached to the CRM housing 390 to allow for the physical and electrical attachment of the intracardiac lead system conductors to the CRM circuitry 310.

The CRM circuitry 310 may be configured as a programmable microprocessor-based system, with circuitry for detecting sleep in addition to providing pacing therapy to the heart. Cardiac signals may be detected by the detector circuitry 360 and delivered to the pacemaker control system 350. Pace pulses controlled by the pacemaker control 350 and generated by the pulse generator 340 are delivered to the heart to treat various arrhythmias of the heart.

The memory circuit 316 may store parameters for various device operations involved in sleep detection and/or cardiac pacing and sensing. The memory circuit 316 may also store data indicative of sleep-related signals received by components of the CRM circuitry 310, such as the impedance drive/sense circuitry 330, the cardiac signal detector system 360, and the accelerometer 335.

The sleep detection circuitry 320 receives signals derived from the cardiac signal detector system 360, the impedance driver/detector circuitry 330 and the accelerometer 335 to perform operations involving detecting sleep onset and termination according to the principles of the present invention. Historical data storage 318 may be coupled to the sleep detection circuitry 320 for storing historical sleep related data. Such data may be transmitted to an external programmer unit 380 and used for various diagnostic purposes and as needed or desired.

Telemetry circuitry 314 is coupled to the CRM circuitry 310 to allow the CRM 300 to communicate with an external programmer unit 380. In one embodiment, the telemetry circuitry 314 and the programmer unit 380 use a wire loop antenna and a radio frequency telemetric link to receive and transmit signals and data between the programmer unit 380 and telemetry circuitry 314. In this manner, programming commands and data are transferred between the CRM circuitry 310 and the programmer unit 380 during and after implant.

The programming commands allow a physician to set or modify various parameters used by the CRM. These parameters may include setting sleep detection parameters for use during sleep detection, such as which sleep-related signals are to be used for sleep detection and threshold adjustment, and the initial sleep detection thresholds. In addition, the CRM system 300 may download to the programmer unit 380 stored data pertaining to sensed sleep periods, including the amount of time spent sleeping, the time of day sleep periods occurred, historical data on sleep times, and the number of arousals during the sleep periods, for example.

Signals associated with patient activity and posture may be detected through the use of an accelerometer 335 positioned within the housing 390 of the CRM 300. The accelerometer responds to patient activity and the accelerometer signal may be correlated with activity level, workload and/or posture. Signals derived from the accelerometer 335 are coupled to the sleep detection circuitry 320 and may also be used by the pacemaker circuitry for implementing a rate adaptive pacing regimen, for example.

The impedance sense electrode 214, the impedance drive electrode 213, and the impedance driver/detector circuitry 330 are used to detect a voltage signal related to transthoracic impedance. The transthoracic impedance measurement may be used to calculate various parameters associated with respiration. Under the control of the sleep detection circuitry 320, the impedance driver circuitry 332 produces a current that flows through the blood between the impedance drive electrode 213 and the can electrode 309. The voltage at the impedance sense electrode 214 relative to the can electrode 309 changes as the transthoracic impedance changes. The voltage signal developed between the impedance sense electrode 214 and the can electrode 309 is detected by the impedance sense amplifier 334 located within the impedance driver/detector circuitry 330 and is delivered to the sleep detection circuitry 320 for further processing.

Figure 4:
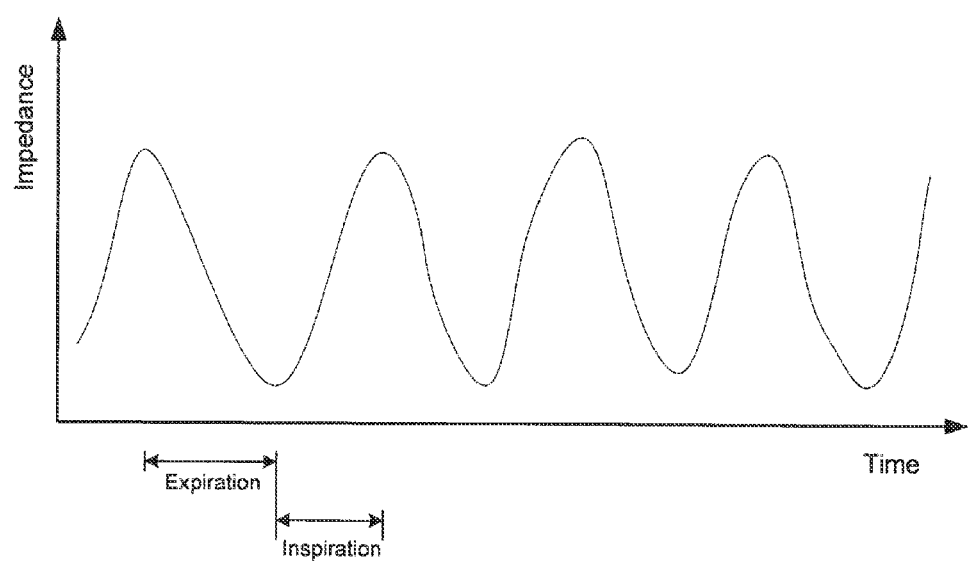
FIG. 4 is a graph of blood impedance used in connection with sleep detection according to an embodiment of the invention.

The voltage signal developed at the impedance sense electrode 214, illustrated in FIG. 4, is proportional to the transthoracic impedance, with the impedance increasing during respiratory inspiration and decreasing during respiratory expiration. The peak-to-peak transition of the impedance measurement, illustrated in FIG. 4, is proportional to the amount of air inhaled in one breath, denoted the tidal volume. The impedance measurement may be further processed to determine the tidal volume, corresponding to the volume of air moved in a breath, or minute ventilation corresponding to the amount of air moved per minute.

In addition to impedance and accelerometer measurements, cardiac signals indicative of heart rate or other cardiac functions may also be used in connection with sleep detection. Turning back to FIG. 3, cardiac signals are sensed through use of the RV-tip and RA-tip sense electrodes 212, 256. More particularly, the right ventricle signal may be detected as a voltage developed between the RV-tip electrode 212 and the can electrode 309. Right ventricle cardiac signals are sensed and amplified by a right ventricle V-sense amplifier 362 located in the detector system 360. The output of the right ventricle V-sense amplifier 362 may be coupled, for example, to a signal processor and A/D converter within the detector system 360. The processed right ventricle signals may be delivered to the pacemaker control 350 and the sleep detection circuitry 320.

Right atrium cardiac signals are sensed and amplified by a right atrial A-sense amplifier 364 located in the detector system 360. The output of the right atrium A-sense amplifier 364 may be processed by signal processing circuitry and received by the pacemaker control 350 and the sleep detection circuitry 320.

The pacemaker control 350 communicates pacing control signals to the pulse generator circuitry 340 for delivering pacing stimulation pulses to the RV-tip and RA-tip electrodes 212 and 256, respectively, according to a preestablished pacing regimen under appropriate conditions.

Figure 5:
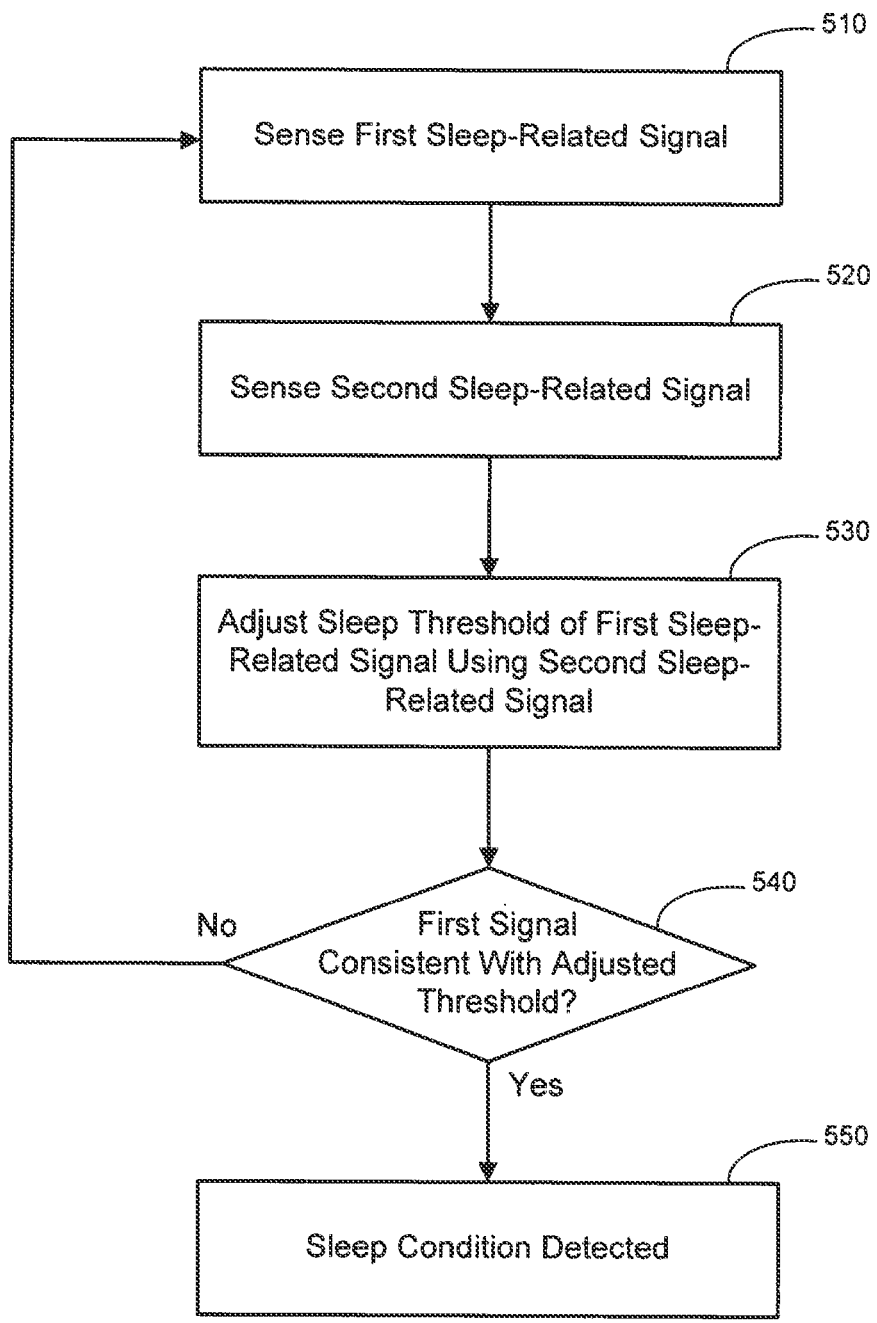
FIG. 5 is a flow graph illustrating a method of detecting sleep according to an embodiment of the invention.

FIG. 5 illustrates a method of detecting sleep according to principles of the invention. A sleep threshold associated with a first sleep-related signal is established. The sleep threshold may be determined from clinical data of a sleep threshold associated with sleep acquired using a group of subjects, for example. The sleep threshold may also be determined using historical data taken from the particular patient for whom the sleep condition is to be detected. For example, a history of a given patient's sleep times can be stored, and a sleep threshold can be developed using data associated with the patient's sleep time history.

The first sleep-related signal is sensed 510. A second sleep-related signal associated with sleep is sensed 520. The first and the second sleep-related signals may be sensed from sensors implanted in the patient, attached externally to the patient or located nearby the patient, for example. The first and the second sleep-related signals may be any signal associated with the condition of sleep, such as the representative sleep-related signals associated with sleep listed above.

The sleep threshold established for the first sleep-related signal is adjusted using the second sleep-related signal 530. For example, if the second sleep-related signal indicates a high level of activity that is incompatible with a sleep state, the sleep threshold of the first sleep-related signal may be adjusted downward to require sensing a decreased level of the first sleep-related signal before a sleep condition is detected.

If the first sleep-related signal is consistent with sleep according to the adjusted sleep threshold 540, a sleep condition is detected 550. If the first sleep-related signal is not consistent with sleep using the adjusted sleep threshold, the first and the second sleep-related signals continue to be sensed 510, 520 and the threshold adjusted 530 until a condition of sleep is detected 550.

Figure 6:
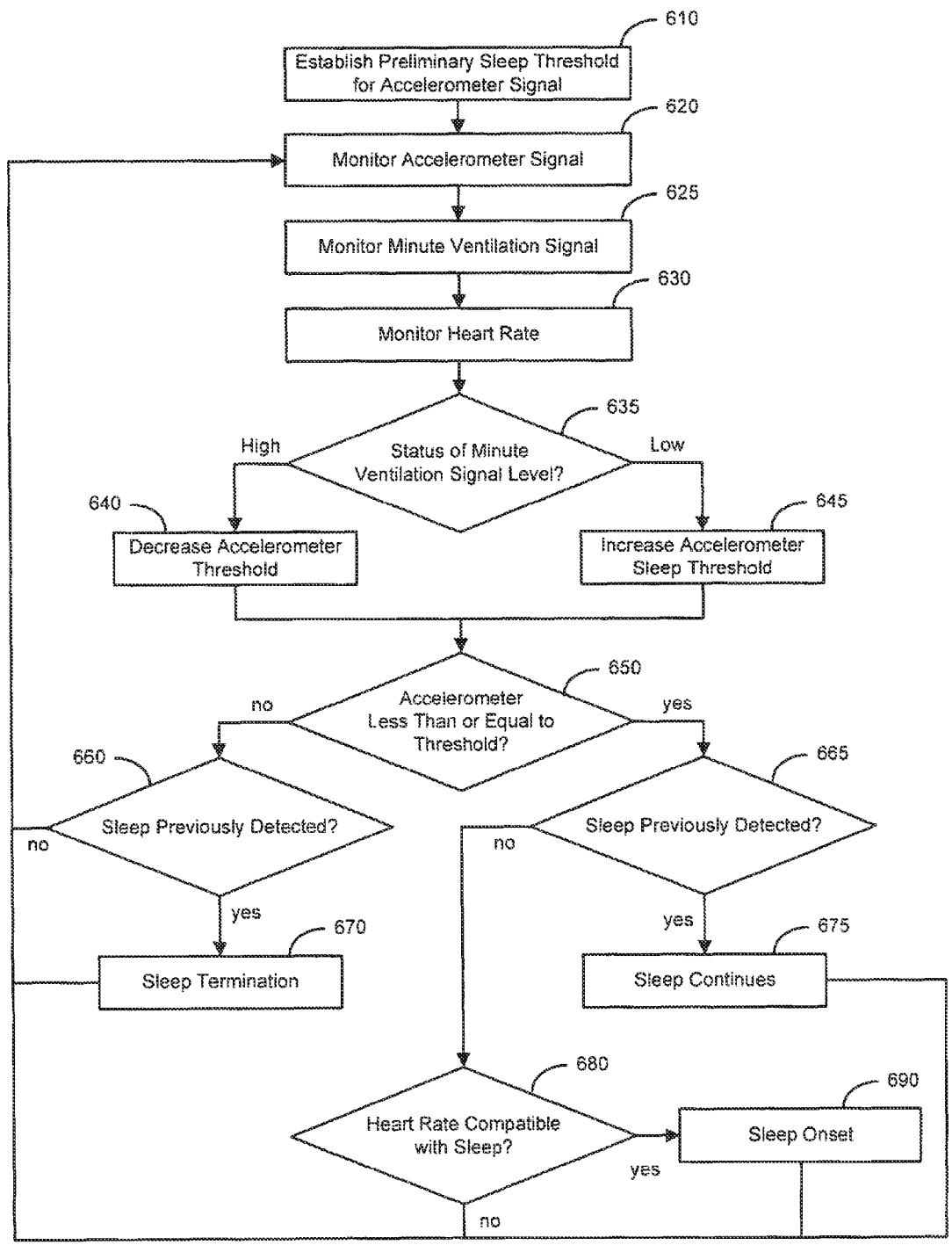
FIG. 6 is a flow graph illustrating a method of detecting sleep using an accelerometer and a minute ventilation sensor according to an embodiment of the invention.

In another embodiment of the invention, illustrated in FIG. 6, an accelerometer and a minute ventilation sensor are used as first and second signals associated with sleep. A preliminary accelerometer signal sleep threshold is determined 610. For example, the preliminary sleep threshold may be determined from clinical data taken from a group of subjects or historical data taken from the patient over a period of time.

The activity level of the patient is monitored using an accelerometer 620 that may be incorporated into an implantable cardiac pacemaker as described above. Alternatively, the accelerometer may be attached externally to the patient. The patient's minute ventilation (MV) signal is monitored 625. The MV signal may be acquired, for example, using the transthoracic impedance method described above using an implantable cardiac device. Other methods of determining the MV signal are also possible and are considered to be within the scope of this invention.

In this example, the accelerometer signal represents the sleep detection signal associated with the sleep threshold. The MV signal is the threshold adjustment signal used to adjust the sleep threshold. Heart rate is monitored 630 in this example to provide a sleep confirmation signal.

Threshold adjustment may be accomplished by using the patient's MV signal to moderate the accelerometer sleep threshold. If the patient's MV signal is low relative to an expected MV level associated with sleep, the accelerometer sleep threshold is increased. Similarly, if the patient's MV signal level is high relative to an expected MV level associated with sleep, the accelerometer sleep threshold is decreased. Thus, when the patient's MV level is high, less activity is required to make the determination that the patient is sleeping. Conversely when the patient's MV level is relatively low, a higher activity level may result in detection of sleep. The use of two sleep-related signals to determine a sleep condition enhances the accuracy of sleep detection over previous methods using only one sleep-related signal to determine that a patient is sleeping.

Various signal processing techniques may be employed to process the raw sensor signals. For example, a moving average of a plurality of samples of each sleep-related signal may be calculated and used as the sleep-related signal. Furthermore, the sleep-related signals may be filtered and/or digitized. If the MV signal is high 635 relative to an expected MV level associated with sleep, the accelerometer sleep threshold is decreased 640. If the MV signal is low 635 relative to an expected MV level associated with sleep, the accelerometer sleep threshold is increased 645.

If the sensed accelerometer signal is less than or equal to the adjusted sleep threshold 650, and if the patient is not currently in a sleep state 665, then the patient's heart rate is checked 680 to confirm the sleep condition. If the patient's heart rate is compatible with sleep 680, then sleep onset is determined 690. If the patient's heart rate is incompatible with sleep, then the patient's sleep-related signals continue to be monitored.

If the accelerometer signal is less than or equal to the adjusted sleep threshold 650 and if the patient is currently in a sleep state 665, then a continuing sleep state is determined and the patient's sleep-related signals continue to be monitored for sleep termination to occur.

If the accelerometer signal is greater than the adjusted sleep threshold 650 and the patient is not currently in a sleep state 660, then the patient's sleep-related signals continue to be monitored until sleep onset is detected 690. If the accelerometer signal is greater than the adjusted sleep threshold 650 and the patient is currently in a sleep state 660, then sleep termination is detected 670.

Figure 7A:
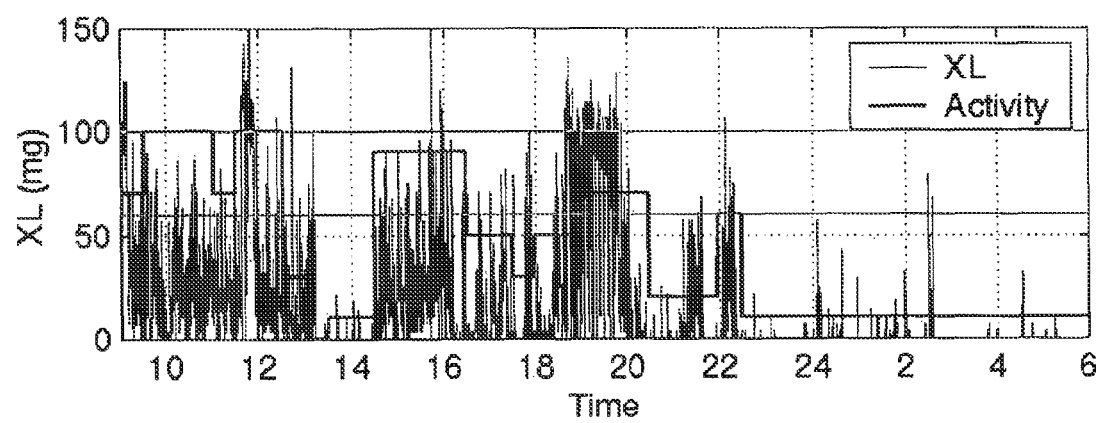
FIG. 7A is a graph of an accelerometer signal indicating patient activity over time that may be used to implement a sleep detection method in accordance with an embodiment of the present invention.
Figure 7B:
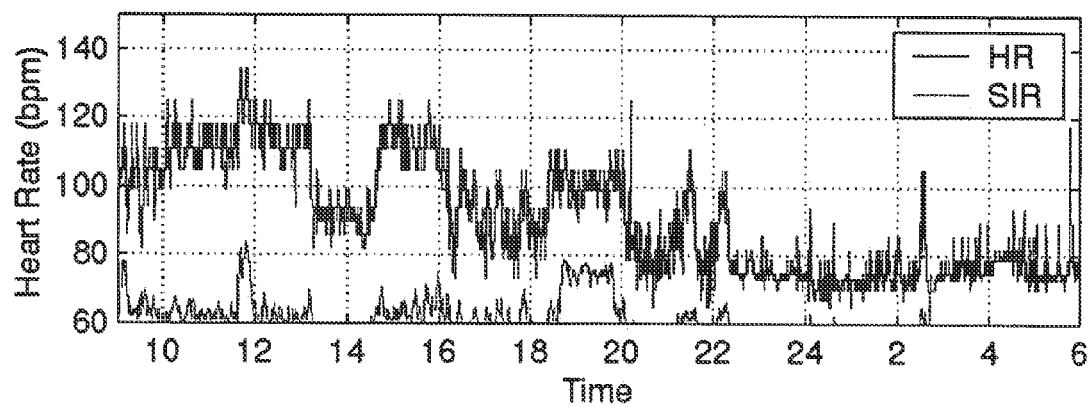
FIG. 7B is a graph of a heart rate signal indicating patient activity over time that may be used to implement a sleep detection method in accordance with an embodiment of the present invention.
Figure 8:
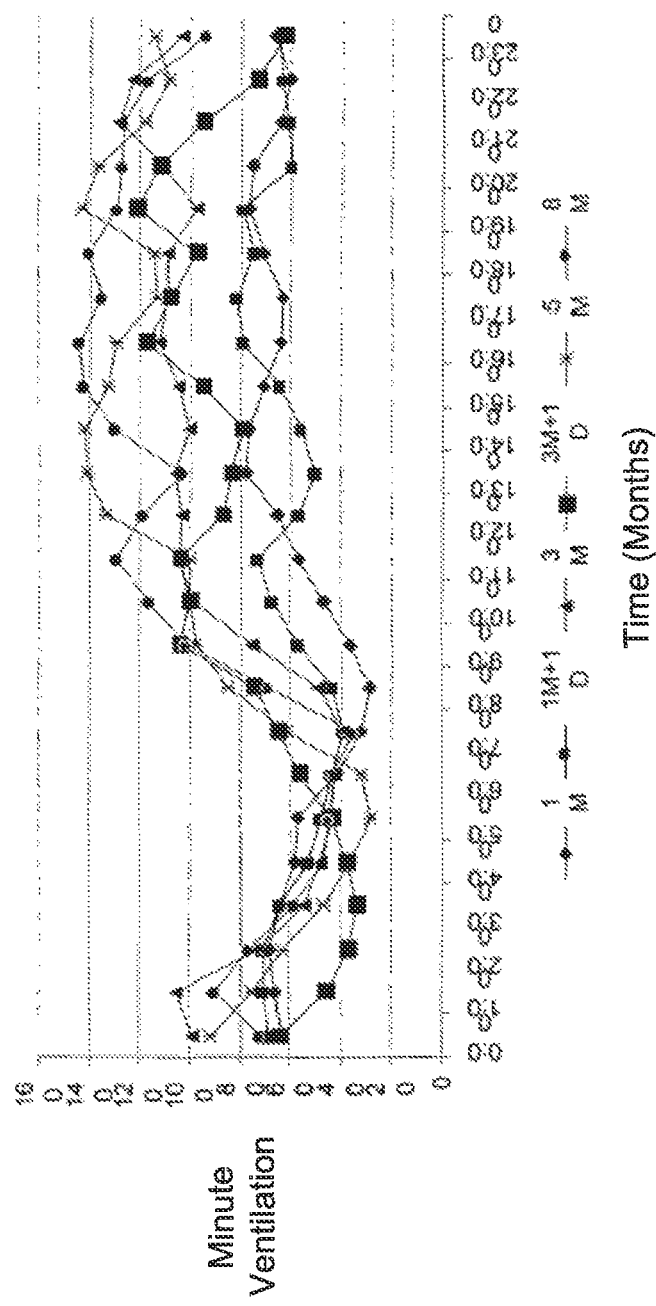
FIG. 8 is a graph of a minute ventilation signal indicating patient respiration that may be used to implement a sleep detection method in accordance with an embodiment of the present invention.
Figure 9:
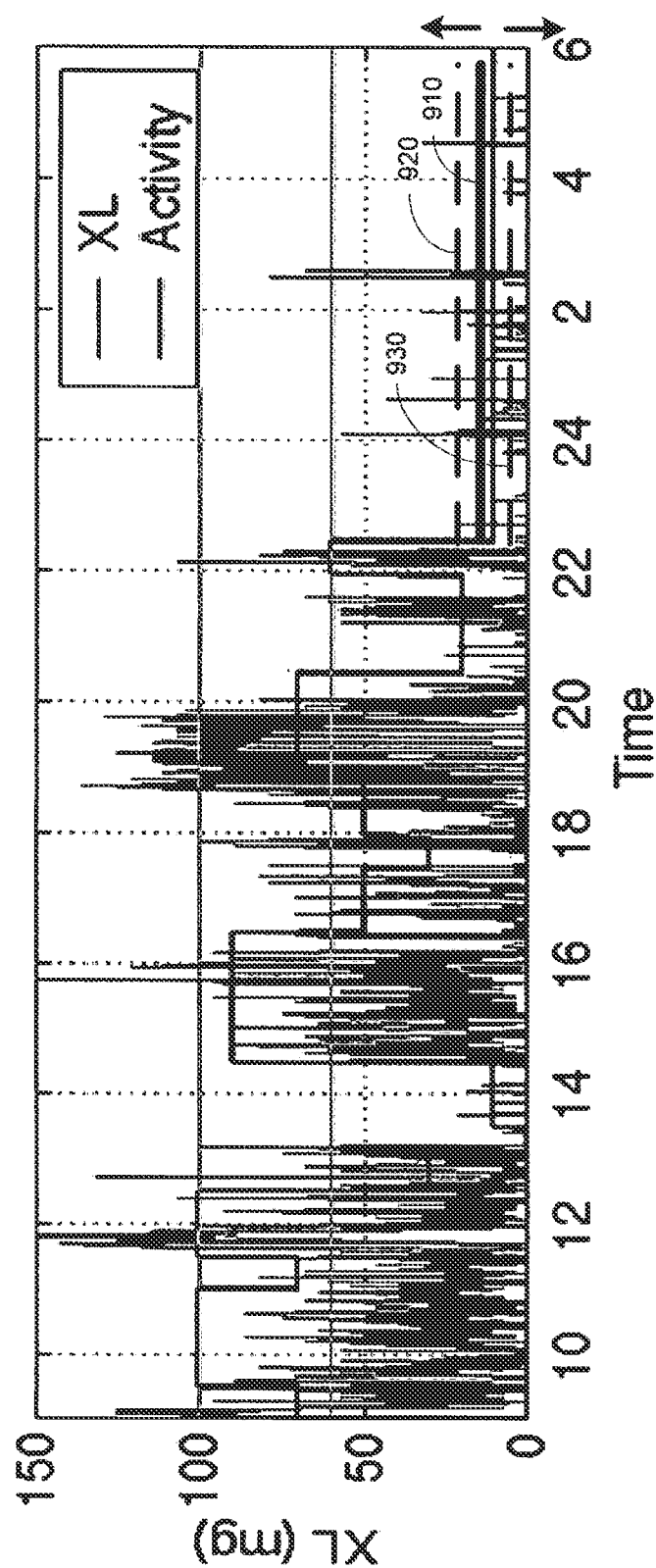
FIG. 9 is a graph illustrating adjustment of an accelerometer sleep threshold using an MV signal in accordance with an embodiment of the invention.

The graphs of FIGS. 7-9 illustrate the adjustment of the accelerometer sleep threshold using the MV signal. The relationship between patient activity and the accelerometer and MV signals is trended over a period of time to determine relative signal levels associated with a sleep condition. FIG. 7A illustrates activity as indicated by the accelerometer signal. The patient's heart rate for the same period is graphed in FIG. 7B. The accelerometer signal indicates a period of sleep associated with a relatively low level of activity beginning at slightly before 23:00 and continuing through 6:00. Heart rate appropriately tracks the activity level indicated by the accelerometer indicating a similar period of low heart rate corresponding to sleep. The accelerometer trends are used to establish a threshold for sleep detection.

FIG. 8 is a graph of baseline trending for an MV signal. Historical data of minute ventilation of a patient is graphed over an 8 month period. The MV signal trending data is used to determine the MV signal level associated with sleep. In this example, a composite MV signal using the historical data indicates a roughly sinusoidal shape with the relatively low MV levels occurring approximately during the period from hours 21:00 through 8:00. The low MV levels are associated with periods of sleep. The MV signal level associated with sleep is used to implement sleep threshold adjustment.

FIG. 9 illustrates adjustment of the accelerometer sleep threshold using the MV signal. The initial sleep threshold 910 is established using the baseline accelerometer signal data acquired as discussed above. If the patient's MV signal is low relative to an expected MV level associated with sleep, the accelerometer sleep threshold is increased 920. If the patient's MV signal level is high relative to an expected MV level associated with sleep, the accelerometer sleep threshold is decreased 930. When the patient's MV level is high, less activity detected by the accelerometer is required to make the determination that the patient is sleeping. However, if the patient's MV level is relatively low, a higher activity level may result in detection of sleep. The use of two sleep-related signals to adjust a sleep threshold for determining a sleep condition enhances the accuracy of sleep detection over previous methods.

Additional sleep-related signals may be sensed and used to improve the sleep detection mechanism described above. For example, a posture sensor may be used to detect the posture of the patient and used to confirm sleep. If the posture sensor indicates a vertical posture, then the posture sensor signal may be used to override a determination of sleep using the sleep detection and threshold adjustment signals. Other signals may also be used in connection with sleep determination or confirmation, including the representative set of sleep-related signals associated with sleep indicated above.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of detecting sleep, comprising:
    sensing a plurality of sleep-related signals;
    storing a relationship that relates sleep detection to the plurality of sleep-related signals, wherein the relationship evaluates a second one of the plurality of the sleep-related signals as a function of a first one of the plurality of the sleep-related signals;
    detecting sleep based on the sensed plurality of sleep-related signals in conjunction with the stored relationship; and
    providing an output signal indicative of an outcome of the sleep detection;
    wherein at least one of storing, detecting and providing is performed at least in part implantably and effectuated at least in part by a processor.

2. The method of claim 1, further comprising:
    transmitting the output signal to another device capable of operating responsively to the output signal.

3. The method of claim 1, further comprising establishing the relationship.

4. The method of claim 3, wherein the relationship is established based on clinical data.

5. The method of claim 3, wherein the relationship is established based on patient data.

6. The method of claim 1, wherein the plurality of sleep-related signals include at least two of a cardiac signal, a respiratory signal, and a patient activity signal.

7. The method of claim 6, wherein the patient activity signal comprises an acceleration signal from an accelerometer.

8. The method of claim 6, wherein the respiration signal comprises a minute ventilation signal from a minute ventilation sensor.

9. The method of claim 6, wherein the cardiac signal is indicative of heart rate.

10. The method of claim 1, wherein the dependence comprises an interrelationship between the first one of the plurality of the sleep-related signals and the second one of the plurality of the sleep-related signals.

11. The method of claim 10, where the relationship includes a threshold for the first one of the plurality of the sleep-related signals, wherein the first one of the plurality of the sleep-related signals is compared to the threshold, and wherein the interrelationship comprises the second one of the plurality of the sleep-related signals influencing the threshold.

12. A sleep detection device, comprising:
    sensors configured to sense a plurality of sleep-related signals; and
    an implantable sleep processor coupled to the sensors, the implantable sleep processor storing a relationship that relates sleep detection to the plurality of sleep-related signals, wherein the relationship defines an inverse relationship between a first one of the plurality of the sleep-related signals and a second one of the plurality of the sleep-related signals, the implantable sleep processor configured to detect sleep based on the sensed plurality of sleep-related signals in conjunction with the stored relationship, and to provide an output signal indicative of an outcome of the sleep detection.

13. The sleep detection device of claim 12, further comprising an output for outputting the output signal to another device capable of operating responsively to the output signal.

14. The device of claim 12, wherein the sensors comprise an accelerometer configured to sense patient activity and transthoracic impedance sensor configured to sense respiration.

15. The device of claim 12, wherein at least one of the sensors is external to the patient.

16. The device of claim 12, wherein the sleep processor is a component of an implantable cardiac therapy device.

17. The method of claim 12, wherein the dependence comprises an interrelationship between the first one of the plurality of the sleep-related signals and the second one of the plurality of the sleep-related signals.

18. The method of claim 17, where the relationship includes a threshold for the first one of the plurality of the sleep-related signals, wherein the first one of the plurality of the sleep-related signals is compared to the threshold, and wherein the interrelationship comprises the second one of the plurality of the sleep-related signals influencing the threshold.

19. A sleep detection device, comprising:
    an accelerometer configured to sense a measure related to patient activity;
    a transthoracic impedance sensor configured to sense a measure related to respiration;
    a heart rate sensor configured to sense a measure related to heart rate;

the measure related to patient activity, the measure related to respiration and the measure related to heart rate comprising sleep-related signals; and an implantable sleep processor coupled to the sensors, the implantable sleep processor storing a relationship that relates sleep detection to at least two of the sleep-related signals, wherein the relationship evaluates a second one of the sleep-related signals as a function of a first one of the plurality of the sleep-related signals, wherein the implantable sleep processor is configured to detect sleep based on the sensed sleep-related signals in conjunction with the stored relationship, and to provide an output signal indicative of an outcome of the sleep detection.

20. The sleep detection device of claim 19, further comprising an output for outputting the output signal to another device capable of operating responsively to the output signal.

\* \* \* \* \*